United States Patent
Bajgrowicz et al.

(10) Patent No.: US 8,349,890 B2
(45) Date of Patent: Jan. 8, 2013

(54) ISOLONGIFOLANYL-DERIVATIVES SUITABLE AS ODORANTS

(75) Inventors: Jerzy A. Bajgrowicz, Zurich (CH); Christopher Furniss, Uster (CH)

(73) Assignee: Givaudan S.A., Vernier (CH)

( * ) Notice: Subject to any disclaimer, the term of this patent is extended or adjusted under 35 U.S.C. 154(b) by 210 days.

(21) Appl. No.: 13/000,697

(22) PCT Filed: Jun. 29, 2009

(86) PCT No.: PCT/CH2009/000223
§ 371 (c)(1),
(2), (4) Date: Dec. 22, 2010

(87) PCT Pub. No.: WO2010/000083
PCT Pub. Date: Jan. 7, 2010

(65) Prior Publication Data
US 2011/0104098 A1    May 5, 2011

(30) Foreign Application Priority Data
Jul. 1, 2008    (GB) .................................. 0812006.5

(51) Int. Cl.
A61K 31/335    (2006.01)
C07D 317/72    (2006.01)

(52) U.S. Cl. ...................................... 514/462; 549/336

(58) Field of Classification Search ................. 514/462; 549/336
See application file for complete search history.

(56) References Cited

U.S. PATENT DOCUMENTS

| | | |
|---|---|---|
| 5,260,459 A | 11/1993 | Brunke et al. |
| 5,693,606 A | 12/1997 | Brunke et al. |
| 5,892,062 A | 4/1999 | Pickenhagen et al. |
| 2002/0040167 A1 | 4/2002 | Pickenhagen et al. |
| 2005/0009729 A1 | 1/2005 | Monteleone et al. |
| 2008/0248990 A1 | 10/2008 | Bajgrowicz et al. |
| 2009/0018192 A1 | 1/2009 | Zhang et al. |

FOREIGN PATENT DOCUMENTS

| | | |
|---|---|---|
| EP | 0 543 470 A1 | 5/1993 |
| EP | 0 669 308 A1 | 8/1995 |
| EP | 1 178 105 A2 | 2/2002 |
| EP | 1 496 055 A1 | 1/2005 |
| EP | 1 671 964 A1 | 6/2005 |
| WO | WO 2005/083045 A1 | 9/2005 |
| WO | WO 2006/058450 A2 | 6/2006 |
| WO | WO 2007/030963 A1 | 3/2007 |

OTHER PUBLICATIONS

PCT/CH2009/000223-Written Opinion of the International Searching Authority, Aug. 27, 2009.
PCT/CH2009/000223-International Search Report, Aug. 27, 2009.
GB 08 12 005.5-Great Britain Search Report, Oct. 6, 2008.
Punten, Johannes, et al., "New Woody and Ambery Notes from Cedarwood and Turpentine Oil", Chemistry & Biodiversity, 2004, vol. 1, pp. 1936-1948, XP-002543298.

*Primary Examiner* — Taofiq A Solola
(74) *Attorney, Agent, or Firm* — Curatolo Sidotu Co., LPA; Joseph G. Curatolo; Salvatore A. Sidoti

(57) ABSTRACT

The present invention refers to 5,7-dioxatetracyclo [$9.2.1.0^{1,9},0^{4,8}$]tetradecane derivatives of formula I

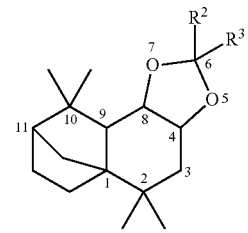

wherein $R^1$-$R^3$ have the same meaning as given in the description.

The invention furthermore refers to their preparation and to perfume compositions and fragrance applications comprising them.

8 Claims, No Drawings

ISOLONGIFOLANYL-DERIVATIVES SUITABLE AS ODORANTS

CROSS REFERENCE TO RELATED APPLICATIONS

This application is a national stage application of International Application No. PCT/CH2009/000223, filed 29 Jun. 2009, which claims priority from Great Britain Patent Application Ser. No. 08 12 006.5, filed 1 Jul. 2008, from which applications priority is claimed, and which are incorporated herein by reference.

The present invention refers to 5,7-dioxatetracyclo[9.2.1.0$^{1,9}$,0$^{4,8}$]tetradecane derivatives having ambery and woody odour notes and their use as odorants. This invention relates furthermore to a method of their production and fragrance compositions comprising them.

In modern perfumery ambery notes play a decisive role. They form the foundation of a lot of perfumes, and it is difficult to imagine a perfume without any woody or ambery notes. Thus there is an ongoing demand for new compounds possessing these odour notes.

Surprisingly, it has now been found that some substituted 5,7-dioxatetracyclo[9.2.1.0$^{1,9}$,0$^{4,8}$]tetradecanes constitute very powerful ambery, woody odorants. In addition the compounds possess a very high substantivity (odour longevity) when applied on animated or unanimated surfaces, such as fabrics, hairs and skin.

Accordingly, the present invention refers in one of its aspects to the use as flavour or fragrance of a compound of formula I

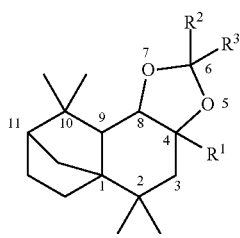

I wherein
$R^1$ is selected from hydrogen, methyl, ethyl and vinyl; and
$R^2$ and $R^3$ are independently selected from hydrogen, methyl, ethyl, and vinyl; or
$R^2$ and $R^3$ together is bivalent radical —(CH$_2$)$_n$—, wherein n is 2 or 3;
with the proviso that the total number of carbon atoms of the compound of formula I is 20 or less, e.g. 16, 17, 18 or 19 carbon atoms.

The compounds of formula I comprise several chiral centres and as such may exist as a mixture of stereoisomers, or they may be resolved as isomerically pure forms.

Resolving stereoisomers adds to the complexity of manufacture and purification of these compounds and so it is preferred to use the compounds as mixtures of their stereoisomers simply for economic reasons. However, if it is desired to prepare individual stereoisomers, this may be achieved according to methods known in the art, e.g. preparative HPLC and GC, crystallization or stereoselective synthesis.

Non-limiting examples are compounds of formula I wherein the relative configuration of the ring system is (1R*, 4S*,8R*,9S*,11R*).

Further, non-limiting examples are compounds of formula I wherein $R^1$ is hydrogen or methyl and $R^2$ is methyl and $R^3$ is hydrogen.

Further, non-limiting examples are compounds of formula I wherein $R^1$ is hydrogen, $R^2$ is methyl or ethyl and $R^3$ is hydrogen or methyl, and compounds of formula I wherein $R^1$ is methyl, $R^2$ is methyl or ethyl and $R^3$ is hydrogen or methyl.

In particular embodiments are compounds of formula I selected from the list consisting of 2,2,6,6,10,10-hexamethyl-5,7-dioxatetracyclo[9.2.1.0$^{1,9}$,0$^{4,8}$] tetradecane (Ia); 6-ethyl-2,2,4,10,10-pentamethyl-5,7-dioxatetracyclo[9.2.1.0$^{1,9}$,0$^{4,8}$] tetradecane (Ib); 2,2,10,10-tetramethyl-5,7-dioxatetracyclo[9.2.1.0$^{1,9}$,0$^{4,8}$]tetradecane (Ic); 2,2,6,10,10-pentamethyl-5,7-dioxatetracyclo[9.2.1.0$^{1,9}$,0$^{4,8}$] tetradecane (Id); 6-ethyl-2,2,10,10-tetramethyl-5,7-dioxatetracyclo[9.2.1.0$^{1,9}$,0$^{4,8}$] tetradecane (Ie); 2,2,4,10,10-pentamethyl-5,7-dioxatetracyclo[9.2.1.0$^{1,9}$, 0$^{4,8}$] tetradecane (If); 2,2,4,6,10,10-hexamethyl-5,7-dioxatetracyclo[9.2.1.0$^{1,9}$,0$^{4,8}$]tetradecane (Ig); and 2,2,4,6,6,10,10-heptamethyl-5,7-dioxatetracyclo[9.2.1.0$^{1,9}$, 0$^{4,8}$]tetradecane (Ih).

The compounds of formula I may be used alone, as mixtures thereof, or in combination with a base material. As used herein, the "base material" includes all known odorant molecules selected from the extensive range of natural products and synthetic molecules currently available, such as essential oils, alcohols, aldehydes and ketones, ethers and acetals, esters and lactones, macrocycles and heterocycles, and/or in admixture with one or more ingredients or excipients conventionally used in conjunction with odorants in fragrance compositions, for example, carrier materials, and other auxiliary agents commonly used in the art.

As used herein, "fragrance composition" means any composition comprising at least one compound of formula I and a base material, e.g. a diluent conventionally used in conjunction with odorants, such as dipropyleneglycol (DPG), isopropylmyristate (IMP), triethylcitrate (TEC) and alcohol (e.g. ethanol).

The following list comprises examples of known odorant molecules, which may be combined with the compounds of the present invention:

essential oils and extracts, e.g. tree moss absolute, basil oil, fruit oils such as bergamot oil and mandarine oil, myrtle oil, palmarose oil, patchouli oil, petitgrain oil, jasmine oil, rose oil, sandalwood oil, wormwood oil, lavender oil or ylang-ylang oil;

alcohols, e.g. cinnamic alcohol, cis-3-hexenol, citronellol, Ebanol™, eugenol, farnesol, geraniol, Super Muguet™, linalool, menthol, nerol, phenylethyl alcohol, rhodinol, Sandalore™, terpineol or Timberol™;

aldehydes and ketones, e.g. anisaldehyde, α-amylcinnamaldehyde, Georgywood™, hydroxycitronellal, Iso E® Super, Isoraldeine®, Hedione®, Lilial®, maltol, Methyl cedryl ketone, methylionone, verbenone or vanillin;

ethers and acetals, e.g. Ambrox™, geranyl methyl ether, rose oxide or Spirambrene™;

esters and lactones, e.g. benzyl acetate, Cedryl acetate, γ-decalactone, Helvetolide®, γ-undecalactone or Vetivenyl acetate;

macrocycles, e.g. Ambrettolide, Ethylene brassylate or Exaltolide®;

heterocycles, e.g. isobutylquinoline.

The compounds according to formula I may be used in a broad range of fragrance applications, e.g. in any field of fine and functional perfumery, such as perfumes, air care products, household products, laundry products, body care products and cosmetics. The compounds can be employed in widely varying amounts, depending upon the specific application and on the nature and quantity of other odorant ingredients. The proportion is typically from 0.001 to 20 weight percent of the application. In one embodiment, compounds of the present invention may be employed in a fabric softener in an amount of from 0.001 to 0.05 weight percent. In another embodiment, compounds of the present invention may be used in fine perfumery in amounts of from 0.1 to 20 weight percent, more preferably between 0.1 and 5 weight percent. However, these values are given only by way of example, since the experienced perfumer may also achieve effects or may create novel accords with lower or higher concentrations.

The compounds as described hereinabove may be employed in a consumer product base simply by directly mixing a compound of formula I, a mixture thereof, or a fragrance composition with the consumer product base, or they may, in an earlier step, be entrapped with an entrapment material, for example, polymers, capsules, microcapsules and nanocapsules, liposomes, film formers, absorbents such as carbon or zeolites, cyclic oligosaccharides and mixtures thereof, or they may be chemically bonded to substrates, which are adapted to release the fragrance molecule upon application of an external stimulus such as light, enzyme, or the like, and then mixed with the consumer product base.

Thus, the invention additionally provides a method of manufacturing a fragrance application, comprising the incorporation of a compound of formula I, as a fragrance ingredient, either by directly admixing the compound to the consumer product base or by admixing a fragrance composition comprising a compound of formula I, which may then be mixed with a consumer product base, using conventional techniques and methods. Through the addition of an olfactory acceptable amount of a compound of the present invention as hereinabove described, or a mixture thereof, the odour notes of a consumer product base will be improved, enhanced or modified.

Thus, the invention furthermore provides a method for improving, enhancing or modifying a consumer product base by means of the addition thereto of an olfactorily acceptable amount of a compound of formula I, or a mixture thereof.

The invention also provides a fragrance application comprising:
a) as odorant a compound of formula I, or a mixture thereof; and
b) a consumer product base.

As used herein, "consumer product base" means a composition for use as a consumer product to fulfill specific actions, such as cleaning, softening, and caring or the like. Examples of such products include fine perfumery, e.g. perfume and eau de toilette; fabric care, household products and personal care products such as laundry care detergents, rinse conditioner, personal cleansing composition, detergent for dishwasher, surface cleaner; laundry products, e.g. softener, bleach, detergent; body care products, e.g. shampoo, shower gel; air care products and cosmetics, e.g. deodorant, vanishing creme. This list of products is given by way of illustration and is not to be regarded as being in any way limiting.

To the best of our knowledge none of the compounds falling within the definition of formula I are described in the literature and are thus novel in their own right.

Accordingly, the present invention refers in a further aspect to compounds of formula I

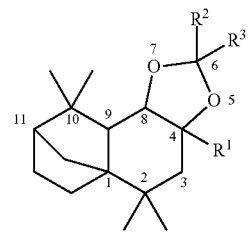

wherein $R^1$ is selected from hydrogen, methyl, ethyl and vinyl; and $R^2$ and $R^3$ are independently selected from hydrogen, methyl, ethyl, and vinyl; or $R^2$ and $R^3$ together is bivalent radical —$(CH_2)_n$—, wherein n is 2 or 3;

with the proviso that the total number of carbon atoms of the compound of formula I is 20 or less, e.g. 16, 17, 18 or 19 carbon atoms.

The compounds of the present invention may be prepared starting from the commercially available isolongifolanone 1 via the hydroxyketone 4. One of many possible syntheses of 4 consists in transformation of isolongifolanone 1 into its enol ester 2a followed by epoxidation and hydrolysis (Scheme 1). The intermediate 4 may be reduced with sodium borohydride or reacted with methyllithium or a Grignard reagent optionally in the presence of a lanthanide salt e.g. cerium chloride. Such obtained diols 5 are transformed into dioxolanes I by usual methods e.g. acid catalyzed acetalization using appropriate ketones or aldehydes with or without azeotropic elimination of water, or transacetalization.

Preparation of compounds of formula I wherein $R^2$ and $R^3$ together is —$(CH_2)_2$— may be carried out via 6,6,-di(halogenomethyl)dioxolanes by electrochemical or metal, e.g. Mg or Zn, mediated cyclisation.

Further particulars as to reaction conditions are provided in the examples.

Scheme 1:

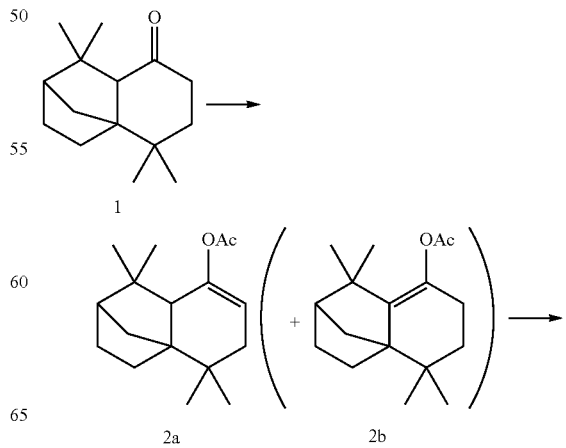

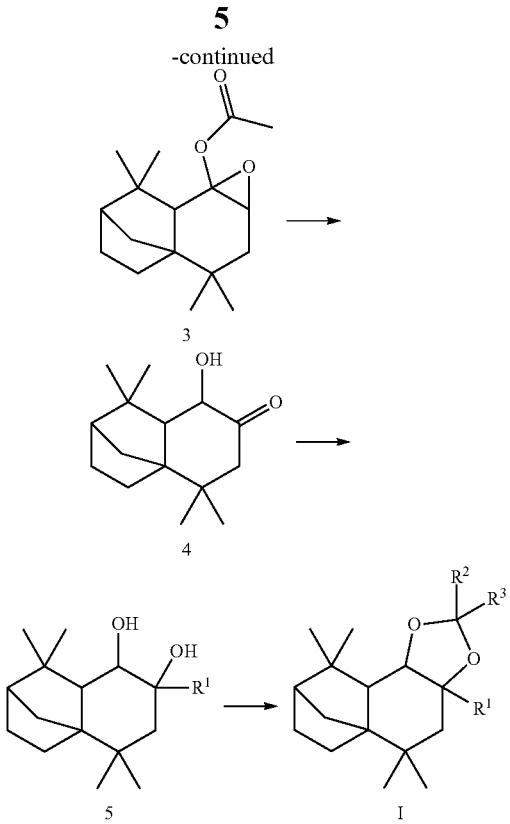

The invention is now further described with reference to the following non-limiting examples. These examples are for the purpose of illustration only and it is understood that variations and modifications can be made by one skilled in the art.

All products described in the Examples were obtained starting from commercially available isolongifolan-8-one (2,2,7,7-tetramethyltricyclo[6.2.1.0$^{1.6}$]undecan-5-one, 1), a mixture of two diastereomeric pairs of enantiomers.

The reported NMR spectra were measured in CDCl$_3$ if not otherwise stated; chemical shifts (δ) are reported in ppm downfield from TMS; coupling constants J in Hz.

Flash chromatography: Merck silica gel 60 (230-400 mesh).

EXAMPLE 1

2,2,6,6,10,10-Hexamethyl-5,7-dioxatetracyclo[9.2.1.0$^{1.9}$,0$^{4.8}$]tetradecane (Ia)

a) 2,2,7,7-Tetramethyltricyclo[6.2.1.0$^{1.6}$]undec-4-en-5-yl acetate (2a)

Concentrated sulphuric acid (0.7 ml) was added to a stirred solution of isolongifolan-8-one (1, 30.0 g, 90% pure, 0.12 mol) in isopropenyl acetate (150 ml). The reaction mixture was heated at reflux for 45 minutes, basified with saturated aqueous solution of sodium bicarbonate (200 ml) and extracted with MTBE (200 ml). The filtrate was washed with water (2×200 ml), dried (Na$_2$SO$_4$), concentrated in vacuo and distilled under reduced pressure to give (at 95° C./<1 mbar) a mixture of 2,2,7,7-tetramethyltricyclo[6.2.1.0$^{1.6}$]undec-4-en-5-yl acetate and 2,2,7,7-tetramethyltricyclo[6.2.1.0$^{1.6}$]undec-5-en-5-yl acetate (2a+2b: 70+25.5%, 30.5 g, 90% yield, pale yellow oil).

An analytical sample of 2a was obtained by flash chromatography (MTBE/hexane 1:50):

$^1$H NMR: δ 5.25 (dt, J=7.0, 1.6, 1H), 2.09-2.16 (m, 1H), 2.10 (s, 3H), 1.92 (m, 1H), 1.76 (ddd, J=16.7, 7.1, 1.2, 1H), 1.71-1.78 (m, 1H), 1.65 (m, 1H), 1.53-1.62 (m, 2H), 1.41 (tt, J=12.5, 4.7, 1H), 1.05-1.16 (m, 2H), 1.04 (s, 3H), 1.02 (s, 3H), 0.98 (s, 3H), 0.92 (s, 3H). $^{13}$C NMR: δ 169.4 (s), 149.6 (s), 112.5 (d), 56.6 (s), 54.0 (d), 48.5 (d), 41.7 (s), 37.7 (t), 36.9 (t), 32.7 (s), 29.6 (t), 28.0 (q), 25.6 (q), 25.0 (q), 24.8 (t) 23.7 (q), 21.3 (q). MS: 262(M$^+$, 3), 221(16), 220(100), 205(18), 177 (33), 150(27), 149(27), 137(24), 136(20), 121(30), 107(26), 91(17), 79(12), 55(35), 43(46), 41(22).

b) 2,2,8,8-Tetramethyl-5-oxatetracyclo[7.2.1.0$^{1.7}$.0$^{4.6}$]dodec-6-yl acetate (3)

A solution of 2,2,7,7-tetramethyltricyclo[6.2.1.0$^{1.6}$]undecen-5-yl acetates described in Example 1a (2a+2b, 30.0 g, 95% pure, 0.11 mol) and MCPBA (36.5 g, 77% pure, 0.16 mol) in methylene chloride (300 ml) was stirred at room temperature (r. t.) for 24 h. An additional portion of MCPBA (10.0 g, 0.045 mol), added after 17 h, was necessary to complete the reaction. The reaction mixture was washed with aqueous sodium hydroxide solution and then water to pH 7 and negative peroxide test (KI paper), concentrated in vacuo and purified by flash chromatography (MTBE/hexane 1:9) to give a 61+37% mixture of 2,2,8,8-tetramethyl-5-oxatetracyclo[7.2.1.0$^{1.7}$.0$^{4.6}$]dodec-6-yl acetate (3) and the isomeric 2,2,8,8-tetramethyl-6-oxatetracyclo[7.2.1.0$^{1.7}$.0$^{5.7}$]dodec-5-yl acetate (14.8 g, 30+18% yield, pale yellow waxy solid). This mixture was used in the next steps without further purification.

An analytical sample of 3 was obtained by a subsequent flash chromatography (MTBE/hexane 1:30):

$^1$H NMR(C$_6$D$_6$): δ 3.08 (dd, J=3.8, 3.0, 1H), 1.94 (d, J=1.8, 1H), 1.91 (dq, J=9.6, 2.3, 1H), 1.57-1.66 (m, 3H), 1.58 (s, 3H), 1.43-1.53 (m, 2H), 1.47 (s, 3H), 1.19 (s, 3H), 1.19 (tdd, J=12.4, 6.3, 3.8, 1H), 1.06 (s, 3H), 0.96 (dddd, J=12.4, 9.3, 6.3, 2.3, 1H), 0.86 (dt, J=9.6, 1.6, 1H), 0.69 (s, 3H). $^{13}$C NMR: δ 169.2(s), 84.1 (s), 56.9 (d), 54.9 (s), 51.9 (d), 48.4 (d), 41.7 (s), 39.2 (t), 36.4 (t), 31.7 (s), 30.1 (t), 29.6 (q), 25.8 (q), 25.7 (q), 25.4 (q), 25.3 (t), 21.3 (q). MS: 278(M$^+$, 2), 236(27), 235(17), 218(22), 207(22), 180(18), 175(16), 163(15), 149 (27), 147(24), 121(33), 109(28), 108(100), 107(52), 93(26), 91(26), 83(39), 80(51), 55(38), 43(81), 41(35).

c) 5-Hydroxy-2,2,7,7-tetramethyltricyclo[6.2.1.0$^{1.6}$]undecan-4-one (4)

2,2,8,8-Tetramethyl-5-oxatetracyclo[7.2.1.0$^{1.7}$.0$^{4.6}$]dodec-6-yl acetate (3, 14.5 g, 61% pure, 0.032 mol) was added at r. t. to a solution of sodium hydroxide (30 g, 0.75 mol) in water (0.75 l) and ethanol (0.75 l). After overnight stirring at r. t., the reaction mixture was neutralized to pH 7 with 2M aqueous HCl solution and extracted with MTBE (2×0.5 l). The combined organic phases were washed with water (2×0.2 l), dried (Na$_2$SO$_4$) and concentrated in vacuo to give crude 5-hydroxy-2,2,7,7-tetramethyltricyclo[6.2.1.0$^{1.6}$]undecan-4-one (4, 13 g, colourless oil, partly solidifying on standing) which was used without further purification in the next steps. Besides two isomeric hydroxyketones, the mixture contained tautomeric forms of the oxidised 4 (diketone).

An analytical sample of 4 was obtained by flash chromatography (MTBE/hexane 1:15): $^1$H NMR: δ 4.04 (dd, J=9.6, 1.0, 1H), 3.46 (sb, 1H), 2.58 (d, J=12.3, 1H), 2.10 (d, J=12.3, 1H), 1.80-1.85 (m, 2H), 1.76 (ddtd, J=12.1, 9.0, 2.8, 0.8 1H), 1.67 (td, J=12.4, 2.9, 1H), 1.32-1.42 (m, 2H), 1.29 (dt, J=10.2, 2.0, 1H), 1.18 (s, 3H), 1.07 (s, 3H), 1.03 (s, 3H), 0.95-1.13 (m, 1H), 0.84 (s, 3H). $^{13}$C NMR: δ 211.9 (s), 75.7 (d), 64.1 (d), 56.4 (s), 50.6 (t), 49.2 (d), 41.1 (s), 39.6 (s), 37.2 (t), 30.1 (t), 28.5 (q), 26.4 (q), 25.9 (q), 25.3 (t), 25.0 (q). MS: 236($M^+$, 10), 180(5), 165(16), 164(100), 163(24), 149(11), 135(10), 121(22), 109(21), 108(24), 107(38), 93(15), 91(14), 79(14), 67(12), 55(18), 43(14), 41(27).

d) 2,2,7,7-Tetramethyltricyclo[6.2.1.0$^{1.6}$]undecane-4,5-diol (5a)

Crude 5-hydroxy-2,2,7,7-tetramethyltricyclo[6.2.1.0$^{1.6}$]undecan-4-one (4, 12 g) from Example 1c was added to a stirred solution of sodium borohydride (2.0 g, 0.052 mol) in isopropanol (40 ml) at r. t. After overnight stirring at 50° C., the reaction mixture was cooled down, 2M aqueous HCl solution (30 ml) and MTBE (100 ml) were successively added and the layers separated. The aqueous layer was extracted with MTBE (100 ml) and the combined organic phases were washed with saturated aqueous solution of sodium bicarbonate (100 ml) and water (100 ml), dried ($Na_2SO_4$) and concentrated in vacuo to afford a mixture of isomeric diols (12 g, viscous white oil, partly solidifying on standing) in which the main diastereoisomeric pair of enantiomers of 2,2,7,7-tetramethyltricyclo[6.2.1.0$^{1.6}$]undecane-4,5-diol (5a) constituted 52% (89% yield starting from 3).

An analytical sample of the latter was obtained by flash chromatography (MTBE/hexane 1:1):

$^1$H NMR (DMSO): δ 4.01 (d, J=2.5, 1H), 3.85 (d, J=7.6, 1H), 3.70 (m, 1H), 3.25 (ddd, J=10.7, 7.6, 3.8, 1H), 1.51-1.62 (m, 4H), 1.49 (dd, J=14.2, 3.8, 1H), 1.40 (dd, J=14.2, 2.1, 1H), 1.15-1.23 (m, 1H), 1.14 (d, J=10.7, 1H), 1.08 (m, 3H), 1.01 (m, 3H), 0.97 (s, 3H), 0.92-1.03 (m, 2H), 0.75 (s, 3H). $^{13}$C NMR: δ 72.0 (d), 70.8 (d), 56.3 (s), 54.0 (d), 49.3 (d), 42.7 (t), 39.9 (s), 37.2 (t), 31.9 (s), 30.8 (t), 29.4 (q), 28.2 (q), 27.8 (q), 25.7 (q), 25.2 (t). MS: 238($M^+$, 10), 223(57), 205(40), 194 (25), 182(100), 177(21), 164(19), 149(18), 137(19), 135(25), 121(45), 109(47), 107(49), 95(35), 93(40), 91(36), 85(30), 81(30), 79(35), 69(38), 67(36), 55(53), 43(43), 41(73).

e) 2,2,6,6,10,10-Hexamethyl-5,7-dioxatetracyclo[9.2.1.0$^{1.9}$, 0$^{4.8}$]tetradecane (Ia)

A solution of diols from Example 1d (3.0 g, ~6.5 mmol of the main diastereomeric pair of enantiomers of 5a), 2,2-dimethoxypropane (4.0 g, 0.38 mol) lithium bromide (0.1 g) and p-toluenesulfonic acid (0.1 g) in THF (40 ml) was stirred at r. t. for 2 h, then poured onto saturated aqueous sodium bicarbonate solution (100 ml) and extracted with MTBE (2×100 ml). The combined organic phases were washed with water (2×100 ml), dried ($Na_2SO_4$), concentrated in vacuo and the residue (3.0 g) purified by flash chromatography (MTBE/hexane 1:20) to afford a mixture of isomeric diols (0.60 g, colourless oil) in which the main diastereoisomeric pair of enantiomers of 2,2,6,6,10,10-hexamethyl-5,7-dioxatetracyclo[9.2.1.0$^{1.9}$, 0$^{4.8}$]tetradecane (Ia) constituted 73% (24% yield).

$^1$H NMR($C_6D_6$): δ 4.18 (q, J=6.6, 1H), 4.06 (dd, J=10.6, 6.6, 1H), 1.71 (dd, J=13.6, 6.6, 1H), 1.64-1.70 (m, 1H), 1.59 (dd, or J=13.6, 6.3, 1H), 1.55-1.57 (m, 1H), 1.49 (s, 3H), 1.43-1.50 (m, 1H), 1.30 (s, 3H), 1.23-1.31 (m, 2H), 1.19-1.23 (m, 1H), 1.16 (s, 3H), 1.13 (s, 3H), 0.97 (dddd, J=11.8, 9.1, 5.1, 2.0, 1H), 0.91 (s, 3H), 0.87-091 (m, 1H), 0.72 (s, 3H). $^{13}$C NMR ($C_6D_6$): δ 107.7 (s), 76.2 (d), 73.8 (d), 57.3 (d), 55.3 (s), 48.7 (d), 40.7 (s), 40.5 (t), 37.3 (t), 32.3 (t), 31.7 (s), 28.6 (2q), 28.4 (q), 28.1 (q), 26.0 (q), 25.6 (q), 25.2 (t). MS: 263($M^+$-15, 37), 221(21), 204(16), 203(100), 147(31), 121(17), 119(28), 109(17), 107(21), 105(17), 95(21), 93(15), 91(19), 79(14), 69(16), 55(22), 43(34), 41(26).

Odour description: ambery, woody, bright, radiant.

EXAMPLE 2

6-Ethyl-2,2,4,10,10-pentamethyl-5,7-dioxatetracyclo[9.2.1.0$^{1.9}$,0$^{4.8}$]tetradecane (Ib)

a) 2,2,4,7,7-Pentamethyltricyclo[6.2.1.0$^{1.6}$]undecane-4,5-diol (5b)

Methyllithium (63 ml of a 1.6M solution in diethyl ether, 0.10 mol) was added over 1 h to a solution of crude 5-hydroxy-2,2,7,7-tetramethyltricyclo[6.2.1.0$^{1.6}$]undecan-4-one (4, 20 g, obtained as in Example 1c) in diethyl ether (200 ml), cooled below 10° C. After 1.5 h stirring, an additional portion of methyllithium (50 ml of a 1.6M solution in diethyl ether, 0.080 mol) was added and stirring continued overnight at room temperature. The reaction mixture was poured onto a stirred mixture of saturated aqueous solution of ammonium chloride (200 ml) and ice (100 g), the phases separated and the aqueous phase extracted with MTBE (200 ml). The combined organic phases were washed with water (3×200 ml), dried ($Na_2SO_4$), concentrated in vacuo and the residue (21 g) purified by flash chromatography (MTBE/hexane 1:3 to 1:2) to afford 2,2,4,7,7-pentamethyltricyclo[6.2.1.0$^{1.6}$]undecane-4,5-diol (5b, 5.7 g, ~46% yield starting from 3, white solid).

$^1$H NMR (DMSO): δ 3.71 (d, J=8.5, 1H), 3.46 (s, 1H), 3.03 (dd, J=10.3, 8.5, 1H), 1.51-1.63 (m, 4H), 1.36 (d, $J_{AB}$=14.2, 1H), 1.34 (d, $J_{AB}$=14.2, 1H), 1.14-1.24 (m, 1H), 1.12 (dd, J=10.3. 2.0, 1H), 1.08 (s, 3H), 1.04 (s, 3H), 1.01 (s, 3H), 0.97 (s, 3H), 0.92-1.03 (m, 2 H), 0.74 (s, 3H). $^{13}$C NMR (DMSO): δ 74.3 (d), 71.3 (s), 55.9 (s), 55.1 (d), 49.1 (t), 48.8 (d), 39.8 (s), 36.8 (t), 32.3 (s), 30.5 (t), 29.2 (q), 28.8 (q), 28.1 (q), 27.6 (q), 25.5 (q), 24.9 (t). MS: 252($M^+$, 0.2), 238(16), 237 (100), 219(35), 194(65), 153(25), 135(37), 121(32), 109(45), 107(55), 99(82), 98(54), 95(28), 93(35), 91(31), 85(47), 83(30), 79(30), 69(33), 67(32), 55(49), 43(86), 41(63).

b) 6-Ethyl-2,2,4,10,10-pentamethyl-5,7-dioxatetracyclo[9.2.1.0$^{1.9}$,0$^{4.8}$]tetradecane (Ib)

A solution of 2,2,4,7,7-pentamethyltricyclo[6.2.1.0$^{1.6}$]undecane-4,5-diol (5b, 1.7 g, 6.6 mmol), propionaldehyde (2.0 g, 33 mmol), lithium bromide (75 mg) and p-toluenesulfonic acid (75 mg) in THF (30 ml) was stirred at r. t. for 1 h, then poured onto saturated aqueous sodium bicarbonate solution (50 ml) and extracted with MTBE (2×50 ml). The combined organic phases were washed with water (2×50 ml), dried ($Na_2SO_4$), concentrated in vacuo and the residue (1.9 g) purified by flash chromatography (MTBE/hexane 1:20) and bulb-to-bulb distillation to give 6-ethyl-2,2,4,10,10-pentamethyl-5,7-dioxatetracyclo[9.2.1.0$^{1.9}$,0$^{4.8}$]tetradecane (Ib, 2+98% mixture of isomeric pairs of enantiomers, 0.83 g, 42% yield, colourless oil).

Main pair of enantiomers: $^1$H NMR($C_6D_6$): δ 4.99 (t, J=5.3, 1H), 3.82 (d, J=8.1, 1H), 1.89 (d, J=14.4, 1H), 1.72 (qd, J=7.6, 5.1, 2H), 1.65-1.73 (m, 1H), 1.56 (m, 1H), 1.50 (td, J=12.2, 3.6, 1H), 1.39 (d, J=14.4, 1H), 1.34 (dd, J=8.1, 2.0, 1H), 1.22-1.32 (m, 2H), 1.19 (s, 3H), 1.16 (s, 3H), 1.10 (s, 3H), 0.96-1.04 (m, 1H), 1.02 (s, 3H), 0.99 (t, J=7.6, 3H), 0.91 (dt, J=9.9, 1.7, 1H), 0.76 (s, 3H). $^{13}$C NMR ($C_6D_6$): δ 103.1 (d), 80.0 (d+s), 58.1 (d), 55.8 (s), 48.8 (d), 47.7 (t), 41.1 (s), 37.4 (t), 32.1 (t), 32.0 (s), 29.5 (t), 28.6 (q), 28.5 (q), 27.4 (q), 26.2 (q), 25.9 (q), 25.3 (t), 9.1 (q). MS: 291($M^+$-1, 0.3), 277(1), 263(13), 235(6), 218(17), 217(100), 161(17), 133

(23), 121(12), 109(17), 107(13), 91(11), 79(8), 69(12), 55(15), 43(19), 41(16).

Odour description: woody, ambery.

EXAMPLE 3

The compounds Ic to Ie have been prepared according to the general procedures given in Examples 1e and 2b starting from 2,2,7,7-tetramethyltricyclo[6.2.1.0$^{1.6}$]undecane-4,5-diol (5a) and the compounds If to Ih starting from 2,2,4,7,7-pentamethyltricyclo[6.2.1.0$^{1.6}$]undecane-4,5-diol (5b).

Compound Ic:
$^1$H NMR: δ 5.08 (s, 1H), 4.77 (s, 1H), 4.15 (dd, J=10.1, 6.7, 1H), 4.04 (q, J=6.7, 1H), 1.77 (dd, J=13.8, 6.0, 1H), 1.71 (dd, J=13.8, 6.7, 1H), 1.68-1.76 (m, 1H), 1.65-1.68 (m, 1H), 1.62 (td, J=12.2, 3.6, 1H), 1.44 (dq, J=10.1, 6.6, 1H), 1.37 (tdd, J=12.4, 5.4, 4.1, 1H), 1.06-1.14 (m, 3H), 1.08 (s, 3H), 1.06 (s, 3H), 0.97 (s, 3H), 0.89 (s, 3H). $^{13}$C NMR: δ 93.3 (t), 75.2 (d), 74.9 (d), 55.2 (d), 55.1 (s), 48.4 (d), 40.6 (s), 39.5 (t), 37.1 (t), 31.9 (t), 31.6 (s), 28.4 (q), 27.9 (2q), 25.5 (q), 24.9 (t). MS: 250(M$^+$, 5), 236(16), 235(100), 205(30), 194(97), 189(26), 149(17), 135(15), 121(30), 109(19), 107(31), 105(27), 93(26), 91(31), 79(25), 69(25), 67(25), 55(35), 41(45).

Odour description: woody, ambery, dry, powdery, musky.

Compound Id:
$^1$H NMR (C$_6$D$_6$): δ 4.95 (q, J=4.8, 1H), 3.89-3.97 (m, 2H), 1.72 (dd, J=13.4, 7.1, 1H), 1.67 (ddt, J=12.3, 9.1, 3.2, 1H), 1.60 (dd, J=13.4, 6.3, 1H), 1.56 (m, 1H), 1.44 (td, J=12.0, 3.8, 1H), 1.40 (d, J=4.8, 3H), 1.24-1.31 (m, 2H), 1.20 (dd, J=9.9, 1.7, 1H), 1.18 (s, 3H), 1.15 (s, 3H), 0.95 (dddd, J=12.0, 9.1, 5.1, 2.4, 1H), 0.86-0.90 (m, 1H), 0.87 (s, 3H), 0.68 (s, 3H). $^{13}$C NMR (C$_6$D$_6$): δ 100.4 (d), 75.7 (d), 75.6 (d), 58.0 (d), 55.1 (s), 48.6 (d), 40.8 (s), 40.1 (t), 37.3 (t), 32.4 (t), 31.7 (s), 28.4 (2q), 28.0 (q), 25.4 (q), 25.1 (t), 20.8 (q). MS: 264(M$^+$, 1), 263(3), 249(46), 220(6), 208(53), 205(27), 203(100), 165(19), 147(23), 135(17), 121(31), 119(24), 109(26), 107(32), 105(23), 95(25), 93(25), 91(30), 79(24), 69(24), 67(23), 55(34), 43(31), 41(41).

Odour description: ambery, woody, green, radiant, powerful.

Compound Ie:
$^1$H NMR: δ 4.83 (t, J=4.3, 1H), 4.08-4.15 (m, 2H), 1.55-1.79 (m, 5H), 1.68 (qd, J=7.5, 4.3, 2H), 1.45 (dq, J=10.1, 2.2, 1H), 1.38 (tdd, J=12.4, 5.1, 4.3, 1H), 1.07-1.14 (m, 3H), 1.06 (2s, 6H), 0.96 (s, 3H), 0.95 (t, J=7.5, 3 H), 0.89 (s, 3H). $^{13}$C NMR: δ 108.8 (d), 75.3 (2d), 57.1 (d), 55.0 (s), 48.3 (d), 40.5 (s), 39.7 (t), 37.1 (t), 32.2 (t), 31.7 (s), 28.2 (2q), 28.0 (q), 27.2 (t), 25.2 (q), 24.8 (t), 7.9 (q). MS: 277(M$^+$-1, 0.1), 249(10), 204(16), 203(100), 147(26), 119(23), 109(14), 107(16), 105(14), 95(17), 93(1), 91(15), 69(13), 55(18), 41(20).

Odour description: ambery, woody, warm, green, sharp.

Compound If:
$^1$H NMR: δ 5.06 (d, J=1.1, 1H), 4.99 (d, J=1.1, 1H), 3.87 (d, J=8.3, 1H), 1.86 (d, J=14.8, 1H), 1.72 (ddt, J=12.2, 9.2, 2.9, 1H), 1.66-1,70 (m, 1H), 1.63 (td, J=12.2, 3.2, 1H), 1.57 (d, J=14.8, 1H), 1.38 (dq, J=9.8, 2.1, 1H), 1.31 (tdd, J=12.1, 6.0, 3.9, 1H), 1.22 (s, 3H), 1.15 (dd, J=8.3, 2.3 1H), 1.00-1.12 (m, 2H), 1.06 (2s, 6H), 0.98 (s, 3H), 0.88 (s, 3H). $^{13}$C NMR: δ 92.2 (t), 79.7 (d), 79.5 (s), 55.6 (s), 54.0 (d), 48.6 (d), 46.3 (t), 40.5 (s), 37.1 (t), 31.9 (s), 30.9 (t), 28.8 (q), 27.9 (q), 26.6 (q), 26.5 (q), 26.4 (q), 25.3 (t). MS: 263(M$^+$-1, 0.1), 250(17), 249(100), 219(15), 203(26), 163(11), 135(21), 121(19), 119(16), 107(22), 91(18), 69(17), 55(22), 43(32), 41(27).

Odour description: woody, ambery.

Compound Ig:
$^1$H NMR (C$_6$D$_6$): δ 5.16 (q, J=4.9, 1H), 3.80 (d, J=8.1, 1H), 1.88 (d, J=14.4, 1H), 1.69 (ddt, J=12.2, 9.1, 3.1, 1H), 1.55 (m, 1H), 1.51 (td, J=12.2, 3.6, 1H), 1.37 (d, J=4.9, 3H), 1.35-1.40 (m, 2H), 1.22-1.32 (m, 2H), 1.16 (s, 3H), 1.15 (s, 3H), 1.08 (s, 3H), 1.05 (s, 3H), 1.00 (dddd, J=11.8, 9.3, 5.3, 2.4, 1H), 0.91 (dt, J=10.0, 1.7, 1H), 0.77 (s, 3H). $^{13}$C NMR (C$_6$D$_6$): δ 98.8 (d), 80.2 (d), 79.9 (s), 58.3 (d), 55.8 (s), 48.8 (d), 47.7 (t), 41.2 (s), 37.5 (t), 32.0 (t+s), 28.6 (q), 28.4 (q), 27.2 (q), 26.3 (q), 25.9 (q), 25.3 (t), 21.9 (q). MS: 278(M$^+$, 1), 277(6), 264(15), 263(82), 235(14), 219(40), 218(18), 217(100), 163(20), 161(20), 149(16), 135(31), 133(27), 121(36), 109(30), 107(39), 93(24), 91(29), 79(23), 69(27), 67(24), 55(37), 43(61), 41(42).

Odour description: ambery, woody, powdery, creamy, green.

Compound Ih:
$^1$H NMR: δ 3.99 (d, J=8.6, 1H), 1.85 (d, J=14.4, 1H), 1.69 (ddt, J=12.2, 9.1, 3.1, 1H), 1.63-1.66 (m, 1H), 1.63 (td, J=12.2, 3.7, 1H), 1.49 (d, J=14.4, 1H), 1.46 (s, 3H), 1.43 (d, J=0.8, 3H) 1.32-1.43 (m, 3H), 1.38 (s, 3H), 1.04-1.13 (m, 2H), 1.10 (s, 3H), 1.05 (s, 3H), 1.00 (s, 3H), 0.88 (s, 3H). $^{13}$C NMR: δ 107.9 (s), 81.5 (d), 80.4 (s), 56.3 (d), 55.5 (s), 48.6 (t), 48.4 (d), 41.1 (s), 37.2 (t), 32.1 (t), 31.6 (s), 30.0 (q), 29.8 (q), 29.3 (q), 28.6 (q), 28.4 (q), 27.2 (q), 25.8 (q), 24.9 (t). MS: 277(M$^+$-15), 236(18), 235(99), 218(18), 217(100), 161(22), 133(32), 121(22), 109(24), 107(23), 105(19), 91(21), 79(16), 69(19), 55(26), 43(56), 41(28).

Odour description: ambery, woody, β-ionone, green, hot wax.

EXAMPLE 4

Composition for Masculine Cologne

|  | parts by weight |
|---|---|
| Bergamot Oil | 120 |
| Calone 1951 (7-methyl-2H-benzo[b][1,4]dioxepin-3(4H)-one) | 8 |
| Calypsone (6-methoxy-2,6-dimethyloctanal) | 5 |
| Cashmeran (1,1,2,3,3-pentamethyl-2,3,6,7-tetrahydro-1H-inden-4(5H)-one) | 4 |
| Cedar Wood Oil | 10 |
| Cetone Alpha (3-methyl-4-(2,6,6-trimethylcyclohex-2-en-1-yl)but-3-en-2-one) | 10 |
| Dihydro Myrcenol (2,6-dimethyloct-7-en-2-ol) | 40 |
| Ethyl Linalool (3,7-dimethylnona-1,6-dien-3-ol) | 80 |
| Galaxolide S ((4S)-4,6,6,7,8,8-hexamethyl-1,3,4,6,7,8-hexahydrocyclopenta[g]-2-benzopyran) | 60 |
| Iso E Super (3-Acetyl-3,4,10,10-tetramethylbicyclo[4.4.0]decane) | 100 |
| Lavender Oil | 6 |
| Methyl Dihydrojasmonate | 120 |
| Methyl Pamplemousse (6,6-dimethoxy-2,5,5-trimethylhex-2-ene) | 16 |
| Pepperwood (3,7-dimethylocta-1,6-dien-3-yl dimethylcarbamate) | 90 |
| Pharaone (2-cyclohexylhepta-1,6-dien-3-one) 10%/DPG | 4 |
| Radjanol (2-ethyl-4-(2,2,3-trimethylcyclopent-3-enyl)but-2-en-1-ol) | 40 |

| | parts by weight |
|---|---|
| Serenolide (2-(1-(3,3-dimethylcyclohexyl)ethoxy)-2-methylpropyl cyclopropanecarboxylate) | 30 |
| Silvial (3-(4-isobutylphenyl)-2-methylpropanal) | 15 |
| Tropional (α-methyl-1,3-benzodioxole-5-propanal) | 10 |
| White Pepper Oil | 4 |
| Zinarine (2-(2,4-dimethylcyclohexyl)pyridine) 1%/DPG | 8 |
| 2,2,4,6,6,10,10-Heptamethyl-5,7-dioxatetracyclo[9.2.1.0$^{1,9}$,0$^{4,8}$]tetradecane | 20 |
| TOTAL | 800 |

The fragrance presents a fresh bergamot top note with a white pepper character, supported by a woody musky accord. 2,2,4,6,6,10,10-Heptamethyl-5,7-dioxatetracyclo[9.2.1.0$^{1,9}$, 0$^{4,8}$]tetradecane (compound Ih) brings to it volume and intensity, and in particular imparts a clear and vibrant ambery woody facet.

The invention claimed is:

1. A compound of formula I

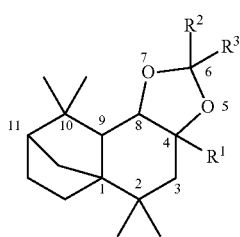

wherein
$R^1$ is selected from hydrogen, methyl, ethyl and vinyl; and
$R^2$ and $R^3$ are independently selected from hydrogen, methyl, ethyl, and vinyl; or
$R^2$ and $R^3$ together is bivalent radical —$(CH_2)_n$—, wherein n is 2 or 3;
with the proviso that the total number of carbon atoms of the compound of formula I is 20 or less.

2. A compound according to claim 1 selected from the from the list consisting of
2,2,6,6,10,10-hexamethyl-5,7-dioxatetracyclo[9.2.1.0$^{1,9}$, 0$^{4,8}$]tetradecane;
6-ethyl-2,2,4,10,10-pentamethyl-5,7-dioxatetracyclo [9.2.1.0$^{1,9}$,0$^{4,8}$]tetradecane;
2,2,10,10-tetramethyl-5,7-dioxatetracyclo[9.2.1.0$^{1,9}$,0$^{4,8}$] tetradecane;
2,2,6,10,10-pentamethyl-5,7-dioxatetracyclo[9.2.1.0$^{1,9}$, 0$^{4,8}$]tetradecane;
6-ethyl-2,2,10,10-tetramethyl-5,7-dioxatetracyclo [9.2.1.0$^{1,9}$,0$^{4,8}$]tetradecane;
2,2,4,10,10-pentamethyl-5,7-dioxatetracyclo[9.2.1.0$^{1,9}$, 0$^{4,8}$]tetradecane;
2,2,4,6,10,10-hexamethyl-5,7-dioxatetracyclo[9.2.1.0$^{1,9}$, 0$^{4,8}$]tetradecane; and
2,2,4,6,6,10,10-heptamethyl-5,7-dioxatetracyclo [9.2.1.0$^{1,9}$,0$^{4,8}$]tetradecane.

3. A method of improving, enhancing or modifying the odor of a consumer product base by means of addition thereto of an olfactory acceptable amount of a compound of formula I as defined in claim 1, or a mixture thereof.

4. A product comprising as odorant a compound of formula I as defined in claim 1, and a consumer product base.

5. A product according to claim 4 wherein the consumer product base is selected from fine fragrance, household products, laundry products, body care products, cosmetic and air care products.

6. A fragrance composition comprising a compound of formula I as defined in claim 1, or a mixture thereof, and a base material.

7. A product comprising as odorant a compound of formula I as defined in claim 2, and a consumer product base.

8. The product according to claim 7 wherein the consumer product base is selected from fine fragrance, household products, laundry products, body care products, cosmetic and air care products.

* * * * *